(12) United States Patent
Lin

(10) Patent No.: US 6,540,683 B1
(45) Date of Patent: Apr. 1, 2003

(54) DUAL-FREQUENCY ULTRASONIC ARRAY TRANSDUCER AND METHOD OF HARMONIC IMAGING

(76) Inventor: Gregory Sharat Lin, 33808 Cassio Cir., Fremont, CA (US) 94555-2016

(*) Notice: Subject to any disclaimer, the term of this patent is extended or adjusted under 35 U.S.C. 154(b) by 0 days.

(21) Appl. No.: 09/953,740

(22) Filed: Sep. 14, 2001

(51) Int. Cl.$^7$ .................................................. A61B 8/00
(52) U.S. Cl. ........................................ 600/447; 600/458
(58) Field of Search ................................. 600/437, 443, 600/447, 459, 458; 310/334–336

(56) References Cited

U.S. PATENT DOCUMENTS

| | | |
|---|---|---|
| 4,490,640 A | 12/1984 | Honda |
| 4,569,231 A | 2/1986 | Carnes et al. |
| 4,603,701 A * | 8/1986 | Chen .......................... 600/459 |
| 4,963,782 A | 10/1990 | Bui et al. |
| 5,115,809 A | 5/1992 | Saitoh et al. |
| 5,163,436 A | 11/1992 | Saitoh et al. |
| 5,381,068 A | 1/1995 | Lorraine |
| 5,410,205 A | 4/1995 | Gururaja |
| 5,415,175 A * | 5/1995 | Hanafy et al. .............. 600/459 |
| 5,438,554 A | 8/1995 | Bolorfor |
| 5,457,353 A | 10/1995 | Thurn et al. |
| 5,488,956 A | 2/1996 | Bartelt et al. |
| 5,526,816 A * | 6/1996 | Arditi .......................... 600/458 |
| 5,578,888 A | 11/1996 | Safabakhsh |
| 5,581,144 A | 12/1996 | Corl et al. |
| 5,699,953 A | 12/1997 | Safabakhsh |
| 5,724,976 A * | 3/1998 | Mine et al. .................. 600/459 |
| 5,740,596 A | 4/1998 | Corl et al. |
| 5,879,303 A | 3/1999 | Averkiou et al. |
| 5,897,500 A * | 4/1999 | Zhao .......................... 600/443 |
| 5,957,852 A | 9/1999 | Hossack et al. |
| 5,976,090 A | 11/1999 | Hanafy et al. |
| 6,025,670 A | 2/2000 | Corl et al. |
| 6,027,448 A | 2/2000 | Hossack et al. |
| 6,040,652 A | 3/2000 | Kaida |
| 6,048,316 A | 4/2000 | Zhao et al. |
| 6,121,718 A | 9/2000 | Mohr |
| 6,384,516 B1 * | 5/2002 | Fraser .......................... 310/334 |

OTHER PUBLICATIONS

B. Ward. "Nonlinear propagation applied to the improvement of resolution in diagnostic ultrasound" J. Acoust. Soc. Am. 1997, vol. 101, No. 1, pp. 143–154.

P.N. Burns et al. "Nonlinear imaging" Ultrasound in Medicine and Biology 2000, vol. 26 (supplement 1), pp. S19–S22.

T.S. Desser et al. "Tissue harmonic imaging techniques: physical principles and clinical applications" Seminars in Ultrsound CT & MR 2001, vol. 22, No. 1, pp. 1–10.

F. Tranquart et al. "Clinical use of ultrasound tissue harmonic imaging" Ultrasound in Medicine and Biology 1999, vol. 25, No. 6, pp. 889–894.

W.T. Shi et al. "Subharmonic imaging with microbubble contrast agents: initial results" Ultrasonic Imaging 1999, vol. 21, No. 2, pp. 79–94.

* cited by examiner

Primary Examiner—Francis J. Jaworski

(57) ABSTRACT

An ultrasonic transducer, method, and system are disclosed for performing ultrasonic harmonic imaging in a medium or a living body. The ultrasonic transducer consists of a linear array of alternating long and short elements. A first set of transducer elements is for transmitting and receiving at a fundamental frequency, and a second set of transducer elements is for receiving second harmonic or subharmonic echoes, each set operating at their respective center frequencies. This dual-frequency ultrasonic transducer is coupled to an ultrasound system wherein transmit beamforming is done at the fundamental frequency, and receive beamforming is done at the second harmonic or subharmonic frequency. When receive beamforming at the fundamental frequency is added, the method enables parallel fundamental, harmonic, compound, and difference imaging. These methods may be utilized to improve ultrasonic harmonic imaging of hard-to-image patients by optimizing the transmission of fundamental-frequency ultrasound beams and the receiving of second harmonic or subharmonic echoes, while minimizing harmonic distortion and signal losses.

14 Claims, 14 Drawing Sheets

DUAL-FREQUENCY ULTRASONIC ARRAY TRANSDUCER AND METHOD OF HARMONIC IMAGING

FIELD OF THE INVENTION

The present invention generally relates to ultrasonic transducers, and more specifically to ultrasonic array transducers capable of transmitting and receiving ultrasonic pulses at two different frequencies.

BACKGROUND OF THE INVENTION

Ultrasonic imaging technology has become an important tool for examining the internal structure of living organisms. In the diagnosis of various medical conditions, ultrasonic imaging is often useful to examine soft tissues within the body to show the structural detail of internal tissues and fluid flow. An important application of ultrasonic imaging is in the detection and identification of various internal structural abnormalities, such as cysts, tumors, abscesses, mineral deposits, blood vessel obstructions, and anatomical defects without physically penetrating the skin.

Ultrasonic images are formed by producing very short pulses of ultrasound using an electro-acoustic transducer, sending the pulses through the body, and measuring the properties (e.g., amplitude and phase) of the echoes from tissues within the body. Focused ultrasound pulses, referred to as "ultrasound beams", are targeted to specific tissue regions of interest in the body. Typically, an ultrasound beam is focused at small lateral and depth intervals within the body to improve spatial resolution. Echoes are received by the ultrasound transducer and processed to generate an image of the tissue or object in a region of interest. The resulting image is usually referred to as a B-scan image.

The echoes from soft tissues and from contrast agents, such as various microbubbles, consist of ultrasound signals at the transmitted frequency (the fundamental frequency) as well as signals at various multiples of the transmitted frequency (harmonics). Apart from the fundamental frequency, the strongest harmonic signal is generally at the second harmonic or twice the fundamental frequency.

Ultrasonic beams are subject to random scattering and distortion as they travel through soft tissues, particularly where there are acoustic interfaces such as between muscle and fat. Collectively referred to as tissue aberrations, these tend to degrade the clarity of the B-scan image. However, harmonic echoes generally exhibit less distortion and diffraction than echoes at the fundamental frequency. Thus, an ultrasound image constructed out of harmonic echoes is often sharper, less hazy, and less distorted.

Recently, harmonic ultrasound imaging has come into widespread use, particularly in viewing deep abdominal organs and the heart. In large patients with thick aberrating layers of fat and muscle, or gastric air pockets, harmonic imaging has been found to provide diagnostically superior ultrasonic images of the liver, kidneys, stomach, uterus, ovaries, and other abdominal organs. Because the heart is surrounded by the lungs which contain aberrating pockets of air, harmonic ultrasound imaging frequently provides clearer images of the cardiac chambers and valves.

Conventional ultrasonic transducers consist of electro-acoustic elements of a particular resonant center frequency. Because lower frequency ultrasonic signals are more penetrating and higher frequency ultrasonic signals enable higher resolution, the choice of a transducer's center frequency is an optimization trade-off between penetration and resolution, depending on the clinical application. Thus, a transducer intended for abdominal use has a lower center frequency of 2.5–5.0 MHz to achieve deep penetration to 18–25 centimeters at lower resolution, while a transducer intended for breast imaging has a higher center frequency of 7–14 MHz to achieve a resolution of 0.2–0.5 mm at reduced penetration. These transducers perform harmonic imaging by having a wide bandwidth such that the transmitted pulses are at the low end of this bandwidth and the harmonic echoes are received at the high end of the same bandwidth. Because a conventional transducer used for harmonic imaging neither transmits nor receives signals at its center frequency, it does not perform efficiently in either transmit or receive. Moreover, transmitting far from a wideband transducer's center frequency introduces undesirable harmonic distortion. These facts limit both the transmitted signal quality and the quality of the resulting harmonic image. They also limit the electro-acoustic efficiency of the transducer, and, hence, penetration.

The present invention, an ultrasonic array transducer for harmonic imaging, consists of alternating elements of different center frequencies—fundamental and harmonic—for transmit and harmonic receive, respectively. Lower-frequency elements are optimally matched to the transmitted fundamental frequency, and higher-frequency elements are optimally matched to harmonic echoes. The transmit elements can also be used for receiving echoes at the fundamental frequency. Thus, this transducer has the novelty of being able to optimally receive echoes at both the fundamental and harmonic frequencies simultaneously. Alternatively, the transducer design may be modified to optimally transmit at a fundamental frequency and receive at a subharmonic frequency (half the fundamental frequency).

SUMMARY OF THE INVENTION

An ultrasonic array transducer is described for performing harmonic imaging. The transducer consists of alternating elements with center frequency at a fundamental frequency and center frequency at twice the fundamental frequency. The former elements are used to transmit and receive at the fundamental frequency, while the latter elements are used to receive harmonic echoes. Center-to-center element spacing is constrained to less than one quarter of the fundamental wavelength.

A method is further described for step-by-step fabrication of said dual-frequency transducer. Alternating elements are milled to half height from the back side before addition of electrical contacts and the acoustic-damping backing layer. Surface layers are then laid on the front side in the usual manner.

A method and system are further described for operating said ultrasonic transducer. In one embodiment of the present invention, the low-frequency elements are used for transmitting and the high-frequency elements are used for receiving. This has the added benefit of eliminating electronic noise generated by transmit-receive switching.

In a preferred embodiment of the present invention, the low-frequency elements are used for both transmitting and receiving at the fundamental frequency, and the high-frequency elements are used for receiving harmonics echoes. This system has the added benefit of being able to generate fundamental, harmonic, compound, and difference images in real time.

In each embodiment, the high-frequency elements may also be used for transmitting (or transmitting and receiving)

at a fundamental frequency and the low-frequency elements may be used for receiving subharmonic echoes.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which.

DETAILED DESCRIPTION OF THE PREFERRED EMBODIMENTS

Figure 1A:
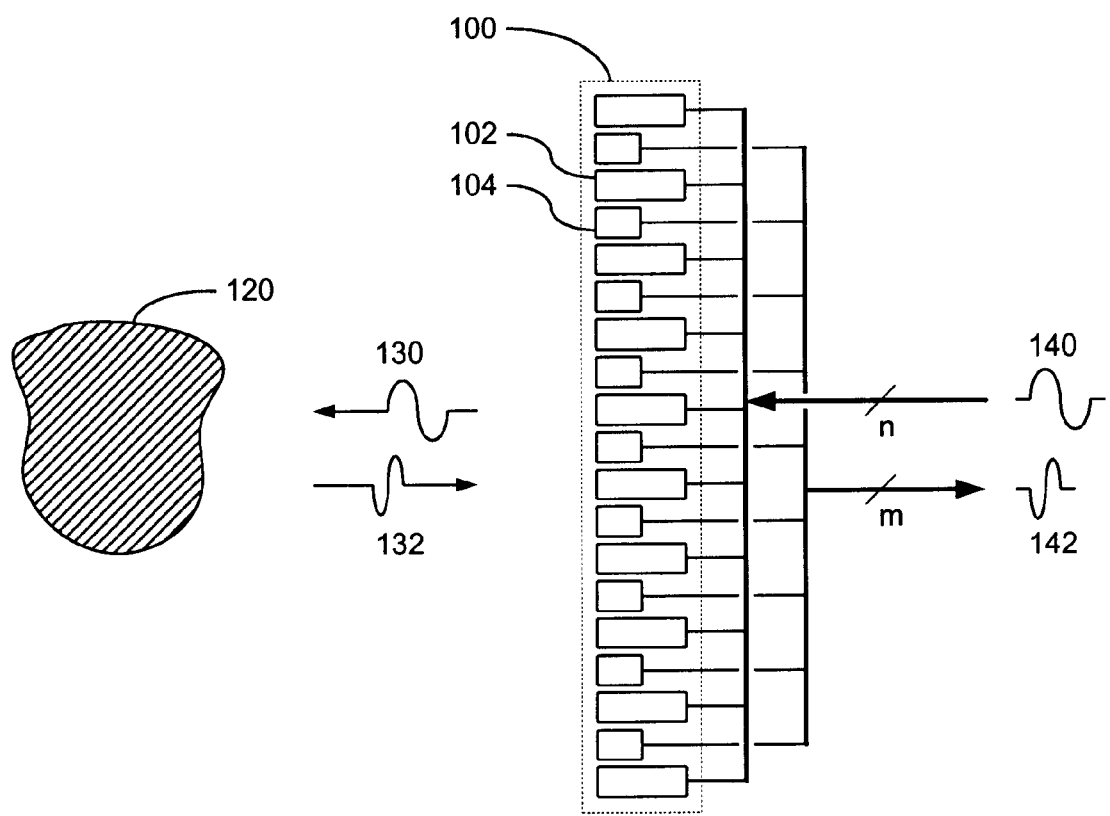
FIG. 1A illustrates a dual-frequency ultrasonic array transducer transmitting a pulse at the fundamental frequency and receiving a second harmonic echo from a tissue reflector.

A dual-frequency ultrasonic array transducer for harmonic imaging, shown in FIG. 1A, comprises an array 100 of individual piezoelectric elements coupled to an ultrasound scanner. The piezoelectric elements consist of long elements 102 whose center frequency is the fundamental transmit frequency, and short elements 104 whose center frequency is twice the fundamental frequency (second harmonic). A transmit pulse 140 at the fundamental frequency is applied to each long element. A transmit beamformer appropriately delays pulses applied across the electronic aperture so as to focus the acoustic beam 130 emitted by the array of long elements. Acoustic beam 130 is transmitted at the fundamental frequency and is reflected by target 120, which may be living tissue in a body or an inanimate structure within a medium which allows ultrasound signals to pass and be reflected. A reflected echo 132 contains pulses at the fundamental frequency, pulses at the second harmonic, and pulses at other frequencies. The long transducer elements 102 optimally receive acoustic signals at the fundamental frequency which is their center frequency. The short transducer elements 104 optimally receive acoustic signals at the second harmonic frequency which is equal to their center frequency. All transducer elements convert the received acoustic signals into electrical pulses. In particular, the short transducer elements 104 preferentially convert second harmonic echoes into electrical pulses 142 at the second harmonic frequency.

Figure 2:
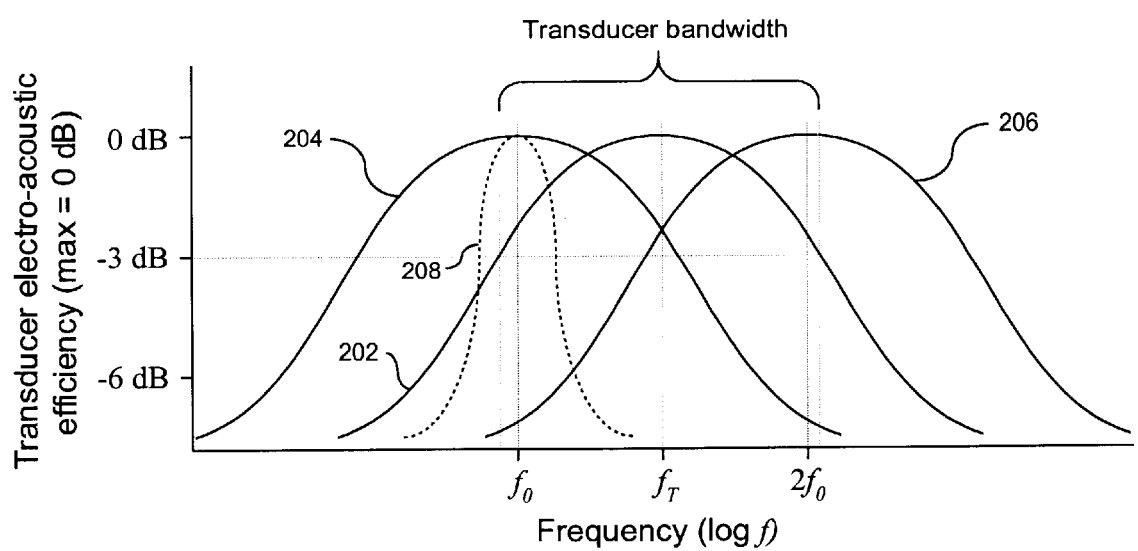
FIG. 2 is a graph of the optimal bandwidths of the transmitted signal, received harmonic signals, and the bandwidth of a conventional wideband transducer.

This method of harmonic signal transduction is advantageous over conventional ultrasound transducers because the usually weaker second harmonic echoes are received by the short transducer elements at their center frequency where electro-acoustic conversion efficiency is maximal, hence where transducer sensitivity is greatest. Similarly, fundamental-frequency pulses are transmitted by the long transducer elements at their center frequency, ensuring acoustic beams without contamination by non-fundamental frequencies and minimal transducer heating. This is in contrast to a conventional ultrasound transducer used in harmonic imaging. The wide bandwidth 202 of a conventional wideband transducer is illustrated in FIG. 2. The center frequency $f_T$ of the conventional transducer is chosen such that the fundamental frequency $f_0$ to be transmitted is within its bandwidth (defined in this illustration as −3 dB down from the peak at the center frequency) at the low-frequency end, and the second harmonic frequency $2f_0$ to be received is also within its bandwidth at the high-frequency end. At $f_0$ and $2f_0$ the transducer is not only less efficient than at its center frequency, but also distorts frequency and phase modulations in the signals by asymmetrically suppressing the lower sideband of the fundamental-frequency signal and the upper sideband of the second harmonic signal. The present invention solves this problem by transmitting fundamental-frequency pulses at the center of the bandwidth 204 of the long elements and receiving second harmonic signals at the center of the bandwidth 206 of the short elements. The transmitted signal itself may be of narrow bandwidth 208, thus, utilizing only a fraction of the available bandwidth of the transmit elements.

Figure 1B:
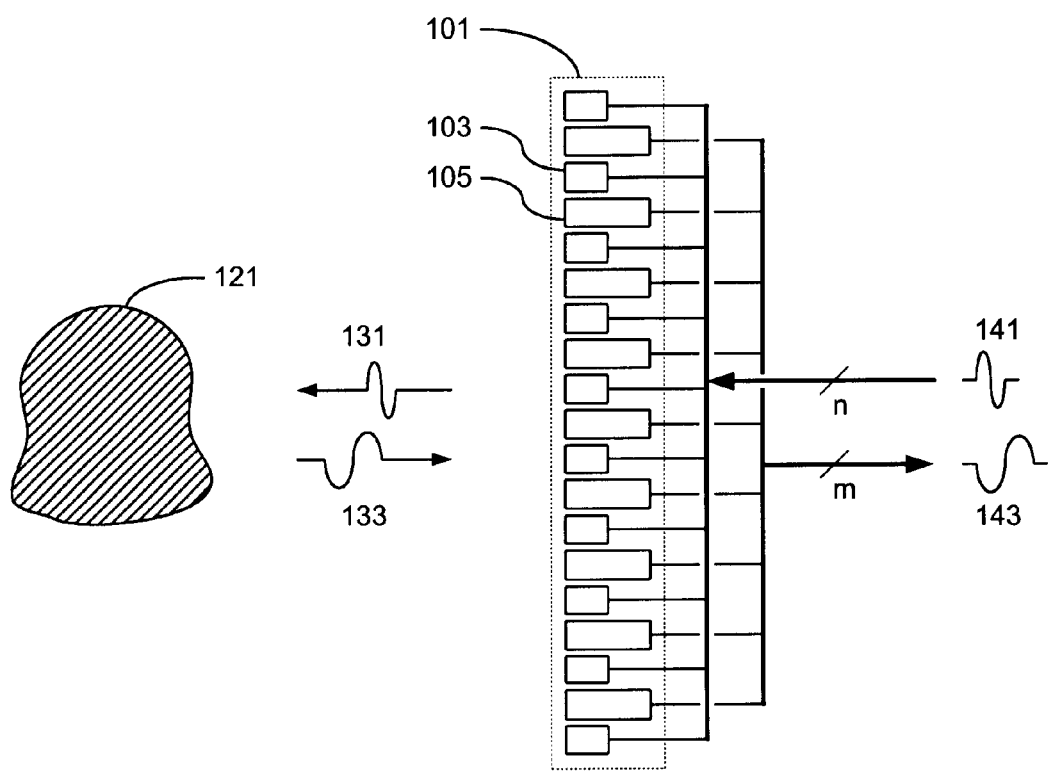
FIG. 1B illustrates a dual-frequency ultrasonic array transducer transmitting a pulse at the fundamental frequency and receiving a subharmonic echo from a tissue reflector.

An ultrasonic transducer for subharmonic imaging, shown in FIG. 1B, comprises an array 101 of individual piezoelectric elements coupled to an ultrasound scanner. The piezoelectric elements consist of short elements 103 whose center frequency is the fundamental transmit frequency, and long elements 105 whose center frequency is half the fundamental frequency (primary subharmonic). A transmit pulse 141 at the fundamental frequency is applied to each short element. A transmit beamformer appropriately delays pulses applied across the electronic aperture so as to focus the acoustic beam 131 emitted by the array of long elements. Acoustic beam 131 is transmitted at the fundamental frequency and is reflected by target 121, which may be living tissue in a body or an inanimate structure within a medium which allows ultrasound signals to pass and be reflected. A reflected echo 133 contains pulses at the fundamental frequency, pulses at the primary subharmonic, and pulses at other frequencies. The short transducer elements 103 optimally receive acoustic signals at the fundamental frequency which is their center frequency. The long transducer elements 105 optimally receive acoustic signals at the subharmonic frequency which is equal to their center frequency. All transducer elements convert the received acoustic signals into electrical pulses. In particular, the long transducer elements 105 preferentially convert subharmonic echoes into electrical pulses 143 at the primary subharmonic frequency.

Figure 3A:
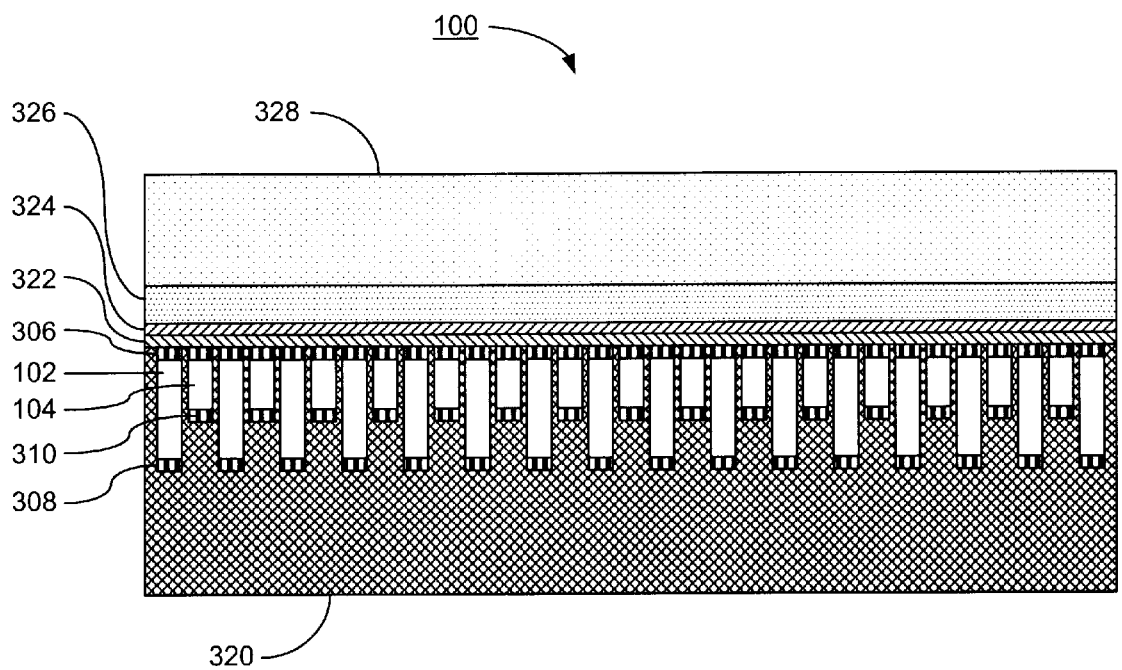
FIG. 3A shows a longitudinal cross-section of a dual-frequency ultrasonic array transducer.

A longitudinal cross-section of the dual-frequency ultrasonic array transducer is shown in FIG. 3A. The drawings are exemplary of a harmonic imaging transducer, but apply equally to the design and fabrication of a subharmonic imaging transducer. Long elements 102 and short elements 104 are arranged in alternating positions along the length of the array. The center-to-center spacing of the elements is optimally chosen to be less than or equal to the wavelength of the upper bandwidth limit of the second harmonic (or higher of the two frequencies of interest) to ensure adequate acceptance angles for beam steering and near-field beam focusing. A common electrical contact 306 is shown on the anterior surface of the transducer elements, and individual electrical contacts 308 and 310 are shown on the posterior surfaces of the long and short elements respectively. The transducer elements are embedded in a backing layer 320 which provides both acoustic damping and structural mounting. The forward surface of the array is coated with two (or more) quarterwave matching layers 322 and 324 whose function is to match the acoustic impedance of the transducer elements to the acoustic lens 326. The thichness of each matching layer is one quarter of the wavelength of the second harmonic (or the higher of two frequencies). Two layers grouped together may also effectively serve as a quarterwave matching layer for signals at the fundamental frequency (or the lower of two frequencies). Ceramic piezoelectric transducers typically have a high acoustic impedance of 15–25 MRayls, much higher than that of soft tissues at approximately 1.5 MRayls. Quarterwave matching layers having intermediate acoustic impedances, reduce acoustic reflectance at the interface between two different materials by reducing the difference in acoustic impedance at that interface. An optional standoff pad 328 puts the skin line a few millimeters away from the transducer elements to eliminate the near-field alternating-line dropout ("picket fence") artifact due to transmitting and/or receiving through every other element in the array. If the center-to-center element spacing and associated element pitch are small enough, the standoff pad may not be necessary.

Figure 3B:
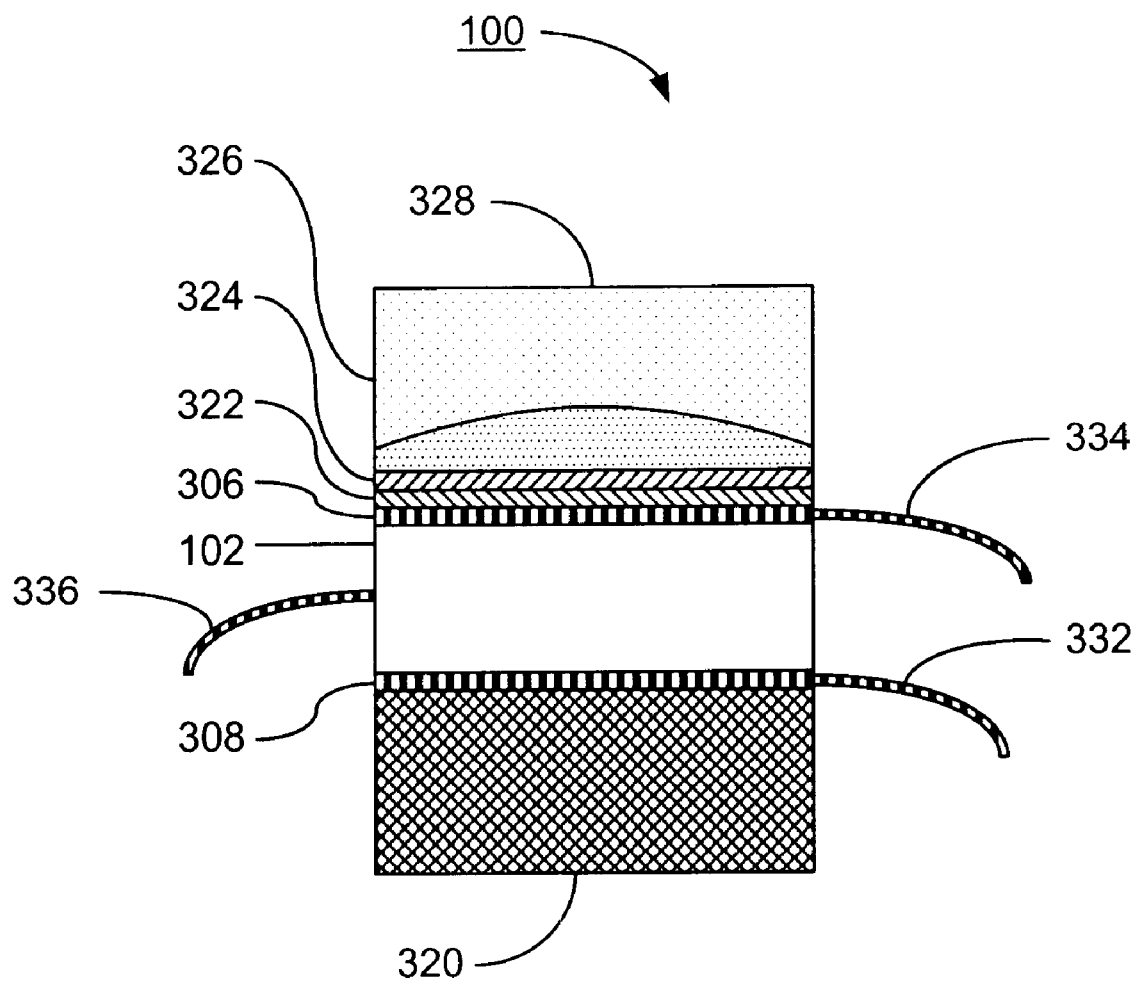
FIG. 3B shows a transverse (elevational) cross-section of a dual-frequency ultrasonic array transducer.

FIG. 3B shows an elevational cross-section of the same transducer. Flex circuit 334 is attached to anterior electrical contact 306. Flex circuit 336 is attached to posterior electrical contact 310 (shown in FIG. 3A). Flex circuit 332 is attached to posterior electrical contact 308.

Figure 4A:
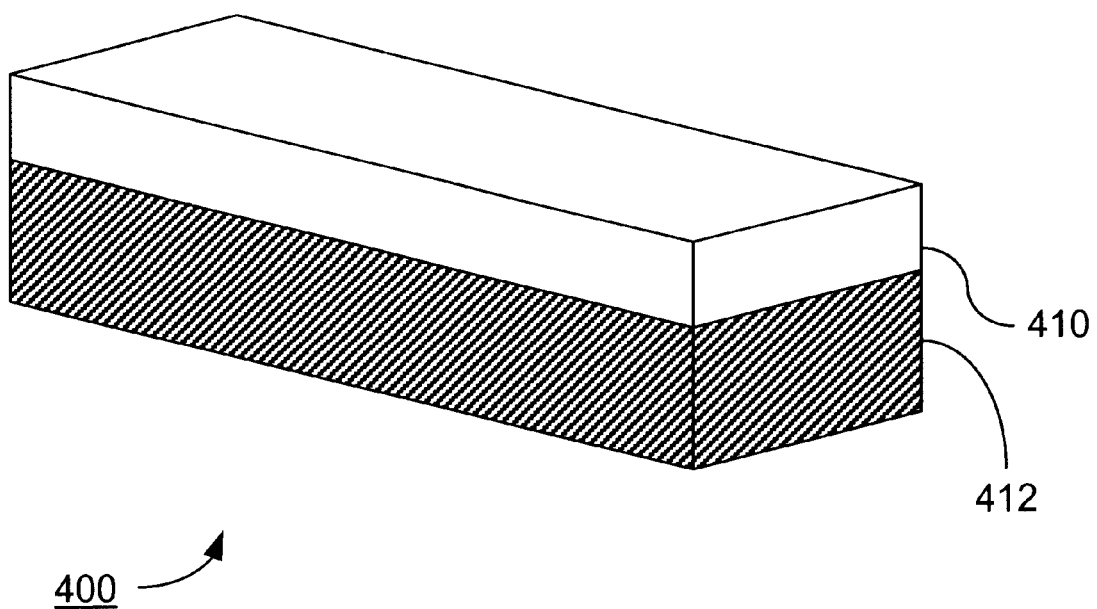
FIG. 4A illustrates a piezoelectric transducer material mounted on a fabrication substrate.
Figure 4B:
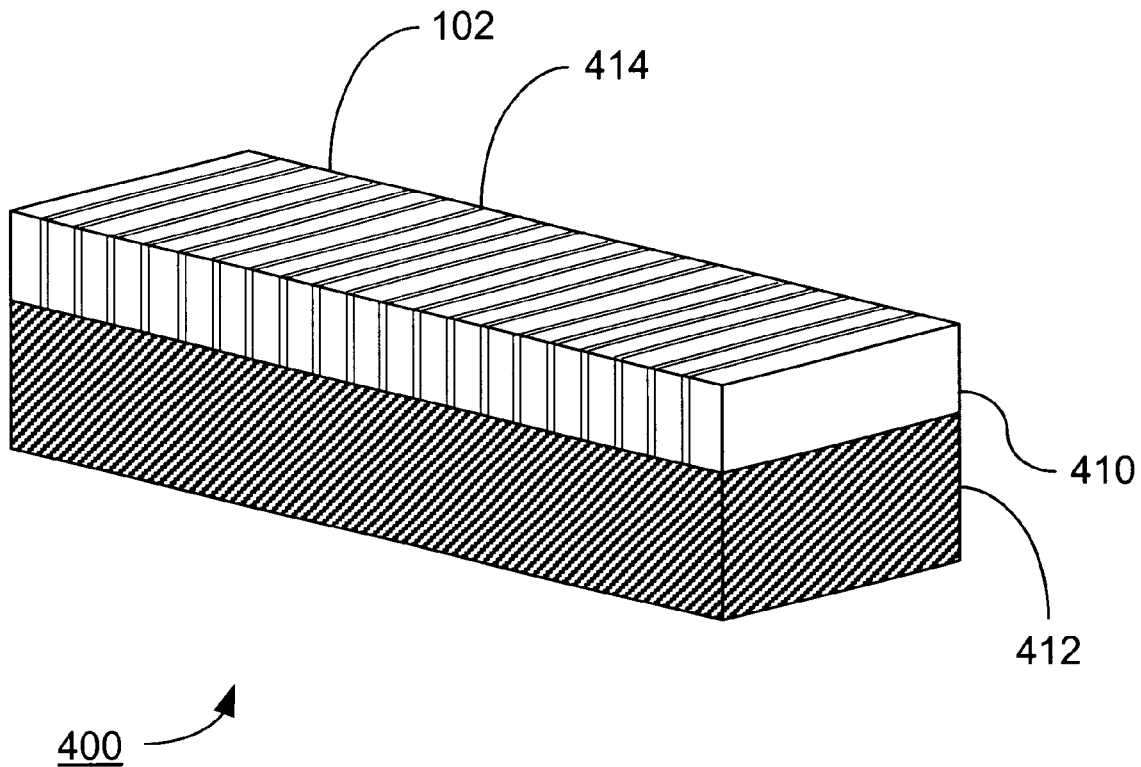
FIG. 4B illustrates a piezoelectric transducer material after dicing into individual elements and filling the kerfs.
Figure 4C:
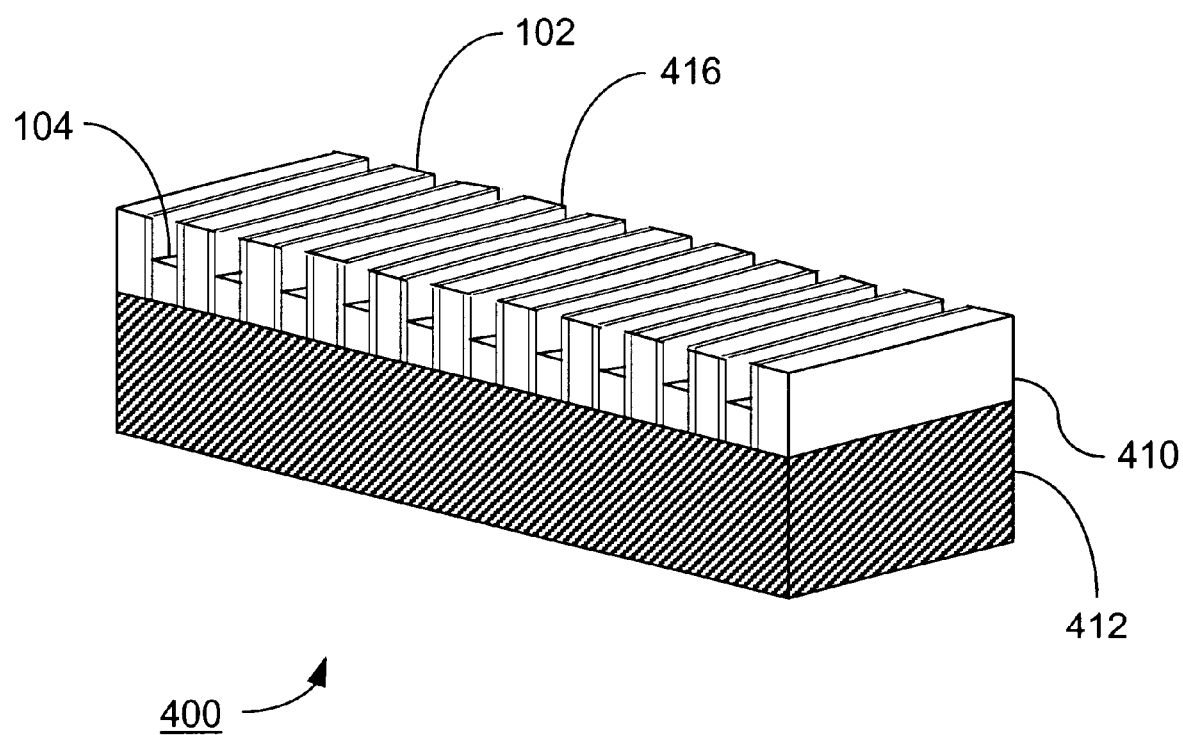
FIG. 4C illustrates a piezoelectric transducer array after milling of alternating elements.
Figure 4D:
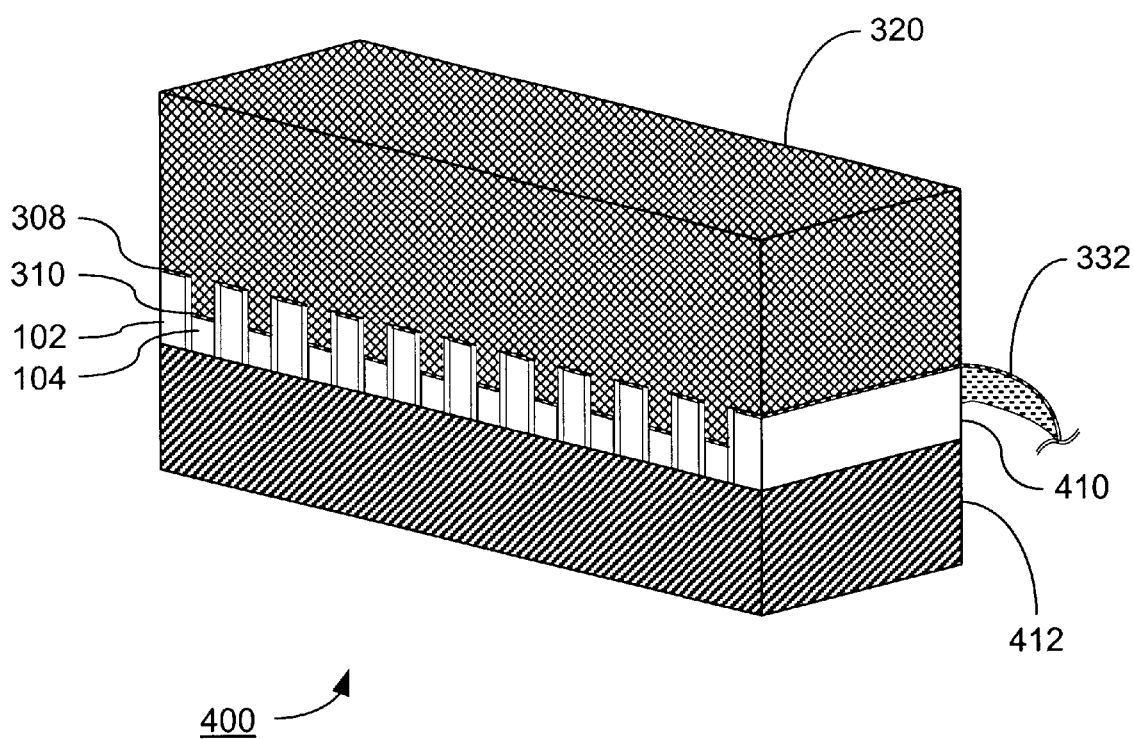
FIG. 4D illustrates a piezoelectric transducer array with attachment of conductive flex circuits and acoustic-damping backing layer.
Figure 4E:
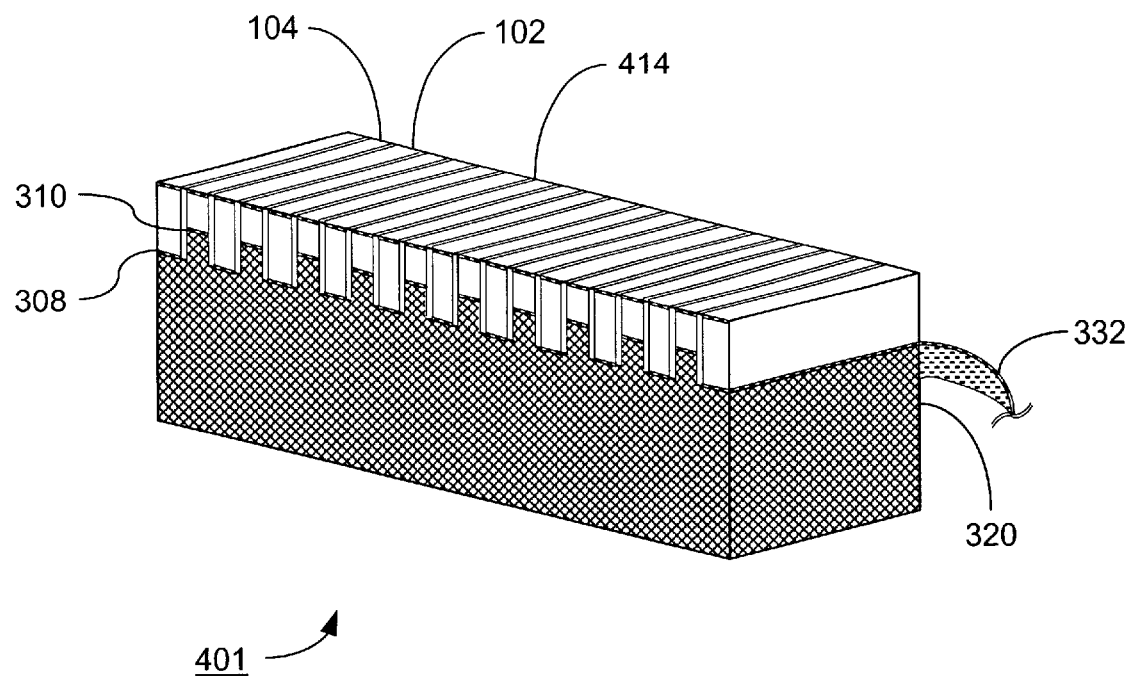
FIG. 4E illustrates a piezoelectric transducer array inverted and with fabrication substrate removed.
Figure 4F:
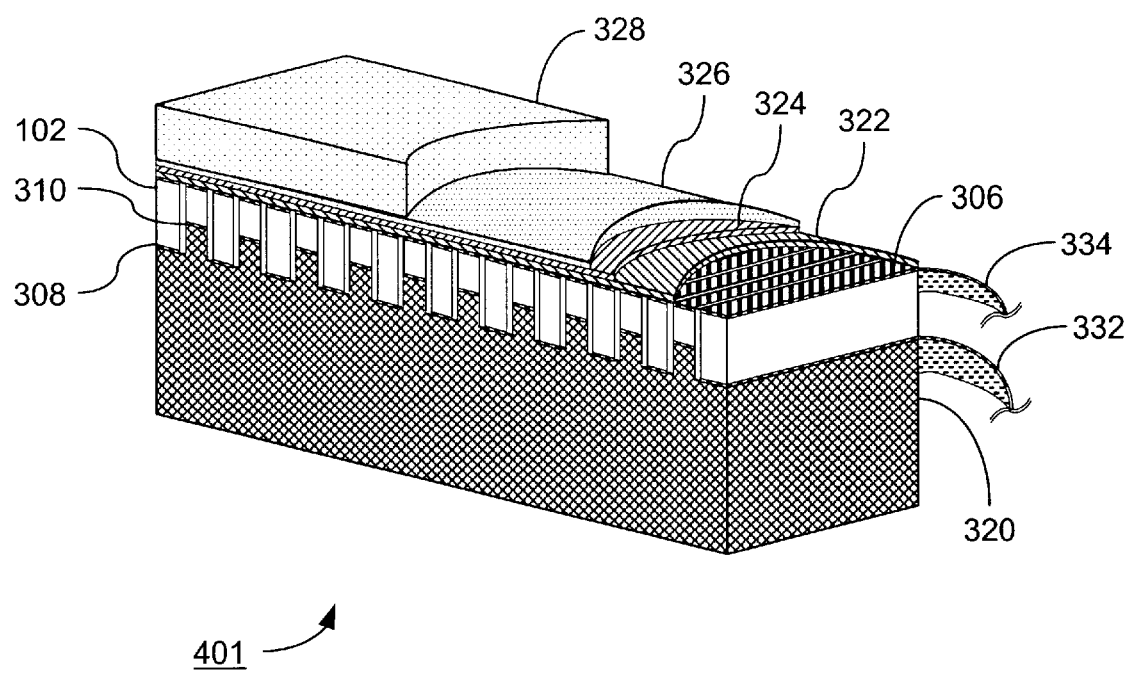
FIG. 4F illustrates a piezoelectric transducer array with attachment of third conductive flex circuit, acoustic matching layers, acoustic lens, and standoff pad in cutaway views.

A method of fabricating the dual-frequency ultrasonic array transducer is illustrated in FIGS. 4A–4F. FIG. 4A shows a mounting block 412 serving as a substrate to support a ceramic piezoelectric block 410. The ceramic piezoelectric block is diced into individual long elements 102 separated by kerfs 414 in FIG. 4B. The kerfs are inter-element spacings that are filled with non-conductive acoustic-damping material. Every other element is milled down to half height to form the short elements 104. Electrical connection layers 308 and 310 are deposited on the rear surfaces of all transducer elements, connected to respective flex circuits (e.g., 332), and then filled in with acoustic-damping backing material 320 as shown in FIG. 4D. The entire block is inverted and the original mounting block 412 is removed as illustrated in FIG. 4E. The anterior electrical connection layer 306, quarterwave matching layers 322 and 324, acoustic lens 326, and optional standoff pad 328 are successively deposited or mounted on top of the array of exposed transducer elements.

Figure 5A:
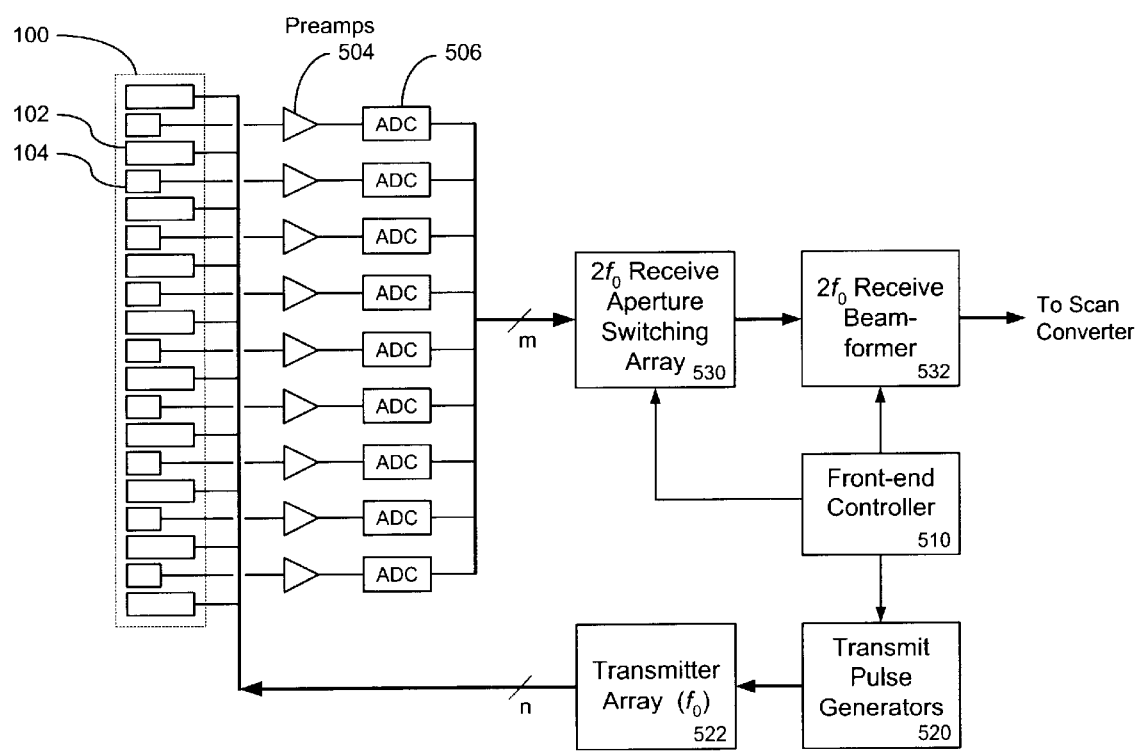
FIG. 5A is a schematic diagram of an embodiment of the front-end circuitry needed for harmonic imaging with the dual-frequency ultrasonic array transducer.

The dual-frequency ultrasonic array transducer is connected to the front end of an ultrasound scanner in a manner described in the block diagram of FIG. 5A. The drawings are exemplary of a harmonic imaging subsystem, but apply equally to the operation of a subharmonic imaging subsystem. In this embodiment, the front-end controller 510 sequences the transmit timing and receive beamforming events to be performed by the front-end circuitry. Transmit pulse generators 520 produce precisely-timed pulse sequences for each active channel in the transmit aperture with a delay profile necessary for electronic beam focusing. The transmitter array 522, driven by timed transmit pulse sequences at the fundamental frequency, sends its output to individual long elements 102 in the transducer. Harmonic echoes are received by individual short elements 104, whose outputs are fed into preamplifiers 504 and analog-to-digital converters 506. Receive aperture switching array 530 selectively passes signals from those channels within the active receive aperture to the receive beamformer 532. The receive beamformer applies specified delays to each channel in the receive aperture to electronically focus the received signals from a particular focal depth, sums them together, and optionally selects those signals within a specified temporal (depth) window from the transmit event. The resulting second harmonic signal is then sent to the scan converter of the ultrasound scanner to be assembled into a viewable image.

Figure 5B:
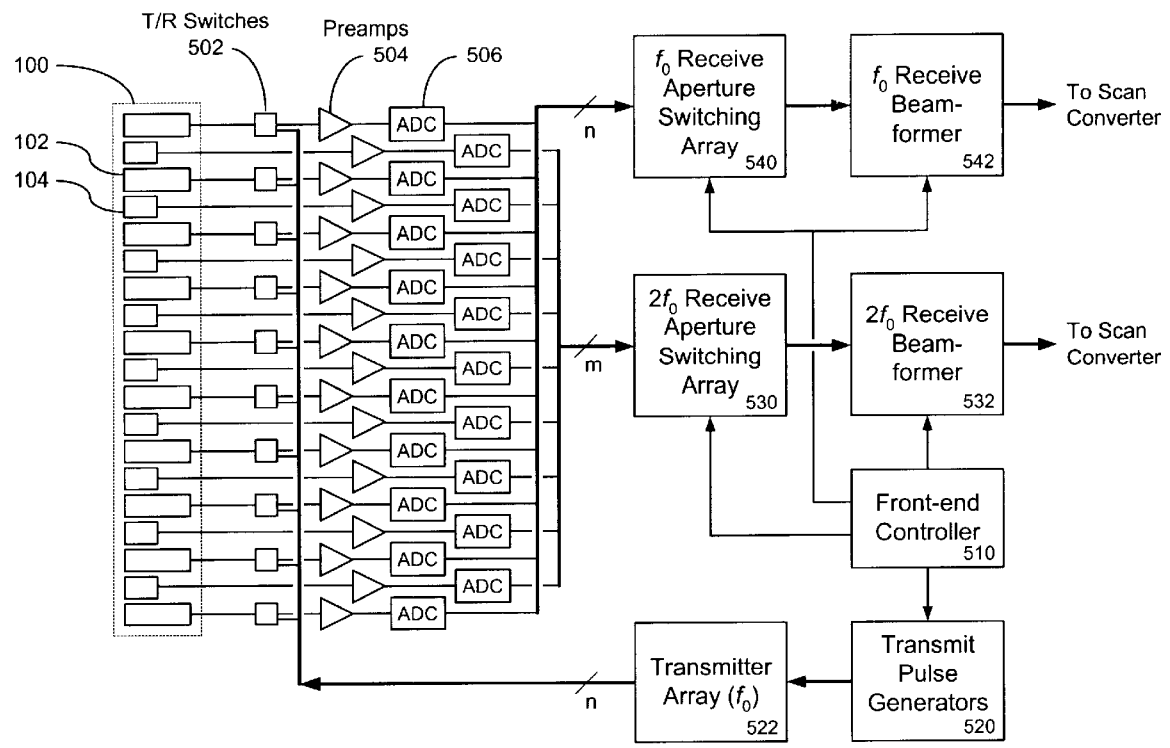
FIG. 5B is a schematic diagram of a preferred embodiment of the front-end circuitry for simultaneous fundamental and harmonic imaging with the dual-frequency ultrasonic array transducer.

In an alternative preferred embodiment of the invention, illustrated in FIG. 5B, transmit-receive (T/R) switches 502 are added to the long elements 102. This enables them to be used for both transmitting and receiving. Additional preamplifiers 504 and analog-to-digital converters 506 are connected to the receive side of each T/R switch. The output of these additional channels is fed into a separate receive aperture switching array 540 and receive beamformer 542 for imaging at the fundamental frequency. The resulting summed fundamental-frequency signal is sent to the scan converter independently of the summed second harmonic signal (described above).

Figure 6:
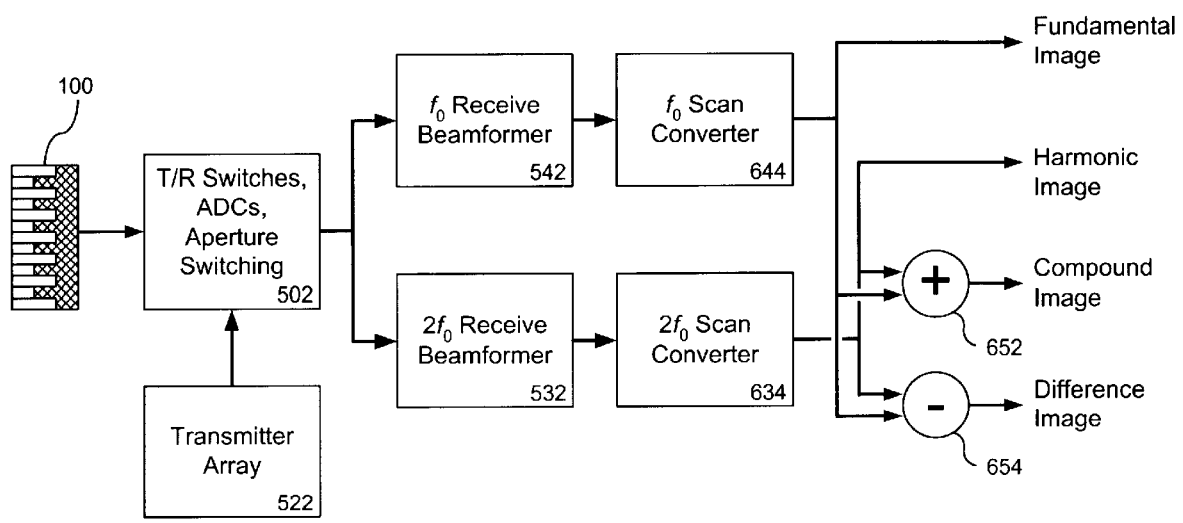
FIG. 6 is a partial block diagram of an ultrasound scanner for generating fundamental, harmonic, compound, and difference ultrasound images.

The block diagram of an ultrasound scanner for simultaneous fundamental-frequency and second harmonic imaging is shown in FIG. 6. Again, the drawings are exemplary of a harmonic imaging system, but apply equally to the concept of a subharmonic imaging system. The output of the fundamental-frequency beamformer 542 is fed into one scan converter 644 to assemble the fundamental-frequency image. The output of the second harmonic beamformer 532 is fed into a second scan converter 634 to assemble the second harmonic image. These images may be displayed individually or side-by-side on the viewing screen of the ultrasound scanner. In addition, the two images may be summed together by summing unit 652 to form a dual-frequency compound image. Compound imaging in general has been found to be useful in reducing speckle and anisotropic reflection artifacts, and in improving image smoothness. The two images may also be subtracted by subtraction unit 654 to form a difference image. Because fundamental-frequency images contain echoes with both linearly-propagated and non-linearly-propagated components, and second harmonic images tend to be comprised primarily of non-linearly-propagated echoes, subtraction imaging may be expected to better visualize the spatial patterns of non-linear propagation and reflection, hence, providing a new parameter for ultrasonic imaging and potential tissue differentiation.

In another alternative embodiment of the invention, the short elements may be used for transmitting at a fundamental frequency and the long elements may be used for receiving at one half the fundamental frequency for the purpose of subharmonic imaging. In addition, the short elements may be used for receiving at the fundamental frequency so as to enable simultaneous fundamental-frequency and subharmonic imaging.

In the foregoing, an ultrasonic array transducer has been described for transmitting at a fundamental frequency and receiving harmonic echoes from a medium or body, the transducer consisting of alternating elements of two different center frequencies. A method has also been described for fabrication of this type of transducer. A method and system have further been described for displaying fundamental, harmonic, compound, and difference images using this transducer. Although the present invention has been described with reference to specific exemplary embodiments, it will be evident that various modifications and changes may be made to these embodiments without departing from the broader spirit and scope of the invention as set forth in these claims. Accordingly, the specification and drawings are to be regarded in an illustrative rather than a restrictive sense.

What is claimed is:

1. A dual-frequency ultrasonic array transducer comprising:
   a first set of piezoelectric elements operable at their center resonant frequency to transmit ultrasonic pulses at a fundamental frequency;
   a second set of piezoelectric elements operable at their center resonant frequency to receive ultrasonic pulses at a second frequency which is either twice the fundamental frequency (harmonic) or half the fundamental frequency (primary subharmonic), wherein said first set of piezoelectric elements and said second set of piezoelectric elements are positioned in a linear alternating sequence;
   an acoustic-damping backing layer;
   electrical contacts bonded to the front and back of each piezoelectric element;
   multiple acoustic impedance matching layers of one-quarter wavelength of the higher said center resonant frequency, wherein the number of said acoustic impedance matching layers is equal to or twice the ratio of the higher of said center resonant frequency to the lower said center resonant frequency; and
   an acoustic lens.

2. A dual-frequency ultrasonic transducer of claim 1 wherein a standoff pad is attached to said acoustic lens.

3. A dual-frequency ultrasonic transducer of claim 1 wherein:
   said first set of piezoelectric elements are operable at their said center resonant frequency to transmit and receive ultrasonic pulses at said fundamental frequency; and
   said ultrasonic pulses received at said fundamental frequency and ultrasonic pulses received by said second set of piezoelectric elements at said second frequency are simultaneously processed by a beamformer and scan converter for simultaneous and/or compound image viewing.

4. A dual-frequency ultrasonic transducer of claim 1 wherein:
   a transmitter/receiver coupled to said dual-frequency ultrasonic transducer is operable to transmit focused beams at one said center resonant frequency and receive focused beams at the other said center resonant frequency;
   a transmit beamformer coupled to said transmitter/receiver is operable to focus transmit pulses by applying appropriate delays to all channels across any given active transmit aperture;
   a receive beamformer coupled to said transmitter/receiver is operable to focus on echoes received from a sequence of focal points within said medium or body by applying appropriate delays to all channels in any given active receive aperture;
   a scan converter coupled to said receive beamformer is operable to convert the geometric coordinate system of the ultrasound vectors into Cartesian coordinates (raster display format); and
   a display subsystem and monitor coupled to said scan converter is operable to display an ultrasound image.

5. A dual-frequency ultrasonic transducer of claim 4 wherein:
   said receive beamformer is further operable to independently focus on echoes received at both said center resonant frequencies;
   said scan converter is further operable to independently convert the geometric coordinate system of the ultrasound vectors received at both said center frequencies into Cartesian coordinates (raster display format); and
   a frame processor coupled to said scan converter is operable to independently assemble a fundamental-frequency image, a second harmonic or subharmonic image, a compound image being a combination of said fundamental-frequency image and said second harmonic or subharmonic image, and/or a difference image being a subtraction of said fundamental-frequency image from said second harmonic or subharmonic image.

6. A method of performing ultrasonic harmonic imaging comprising the steps of:
   (a) generating electrical pulse sequences at a fundamental frequency;
   (b) applying said electrical pulse sequences to a first set of piezoelectric elements with center resonant frequency equal to said fundamental frequency, thereby converting them into acoustic pulses—said first set of piezoelectric elements being arranged in alternating positions with respect to a second set of piezoelectric elements in a dual-frequency ultrasonic linear array transducer;
   (c) introducing said acoustic pulses into an area of a medium or body to be ultrasonically imaged through multiple acoustic impedance matching layers each of whose thickness is one quarter of the wavelength of the higher of the center resonant frequencies of said first set of piezoelectric elements and said second set of piezoelectric elements, wherein the number of said acoustic impedance matching layers is equal to or twice the ratio of the higher of said center resonant frequencies to the lower of said center resonant frequencies;
   (d) receiving echoes at a second harmonic or subharmonic frequency in said second set of piezoelectric elements with center resonant frequency equal to said second harmonic or subharmonic frequency, thereby converting them into a first set of received electrical pulses;
   (e) beamforming said first set of received electrical pulses so as to focus on second harmonic or subharmonic echoes originating from a specified depth zone within said medium or said body;

(f) assembling a second harmonic or subharmonic image by scan converting all image vectors comprised of intensities mapped from said first set of received electrical pulses; and (g) displaying said second harmonic or subharmonic image.

7. A method according to claim 6 further comprising the steps of:

(h) receiving echoes at said fundamental-frequency in said first set of piezoelectric elements, thereby converting them into a second set of received electrical pulses;

(i) beamforming said second set of received electrical pulses so as to focus on fundamental-frequency echoes originating from a specified depth zone with said medium or said body;

(j) assembling a fundamental-frequency image by scan converting all image vectors comprised of intensities mapped from said second set of received electrical pulses; and (k) displaying said fundamental-frequency image.

8. A method according to claim 7 wherein said fundamental-frequency image and said second harmonic or subharmonic image are summed or averaged together pixel-by-pixel to generate a compound image.

9. A method according to claim 7 wherein said fundamental-frequency image and said second harmonic or subharmonic image are subtracted one from another pixel-by-pixel to produce a difference image.

10. An apparatus comprising:

a first plurality of ultrasonic transducer element means for transmitting acoustic energy at a first set of frequencies into an area of a subject being scanned;

a second plurality of ultrasonic transducer element means for receiving acoustic energy at a second set of frequencies from an area of a subject being scanned, wherein said first plurality of ultrasonic transducer element means is laid out in an alternating sequence with respect to said second plurality of ultrasonic transducer element means;

an acoustic-damping backing layer means;

electrical connection means;

acoustic impedance matching means comprised of multiple layers, each having a thickness equal to one quarter of the wavelength of the higher of the center resonant frequencies of said first plurality of ultrasonic transducer element means and said second plurality of ultrasonic transducer element means, and the number of layers being equal to or twice the ratio of the higher and lower center resonant frequencies of said first plurality of ultrasonic transducer element means and said second plurality of ultrasonic transducer element means; and an acoustic lens means.

11. An apparatus of claim 10 wherein:

said first plurality of ultrasonic transducer element means have a center frequency equal to a fundamental frequency; and said second plurality of ultrasonic transducer element means have a center frequency equal to either twice said fundamental frequency (second harmonic) or half said fundamental frequency (primary subharmonic).

12. An apparatus of claim 10 further comprising acoustic stand-off pad means for eliminating near-field acoustic artifacts.

13. An apparatus of claim 10 further comprising:

transmitter means for generating and beamforming transmit pulses at said first set of frequencies to be applied to said first plurality of ultrasonic transducer element means;

a first receiver means for digitizing and beamforming pulses generated by said second plurality of ultrasonic transducer element means received from echoes at said second set of frequencies;

scan converter means for mapping pulses at said second set of frequencies into intensities and arranging the data into a first raster image; and display means for visualizing said first raster image.

14. An apparatus of claim 13 further comprising:

switching means for switching said first plurality of ultrasonic transducer element means between said transmitter means and a second receiver means;

said second receiver means for digitizing and beamforming pulses generated by said first plurality of ultrasonic transducer element means received from echoes at said first set of frequencies;

scan converter means for mapping pulses at said first set of frequencies into intensities and arranging the data into a second raster image;

compound imaging means for averaging said first raster image and said second raster image;

difference imaging means for subtracting said second raster image from said first raster image; and display means for visualizing said second raster image, the compound image, and the difference image.

* * * * *